(12) United States Patent
Keith et al.

(10) Patent No.: US 7,563,460 B2
(45) Date of Patent: Jul. 21, 2009

(54) ENTERIC COATED ORAL PHARMACEUTICAL TO ERODE KIDNEY STONES

(75) Inventors: Alec D. Keith, Hilo, HI (US); William E. Crisp, Paradise Valley, AZ (US)

(73) Assignee: Med Five, Inc., Honolulu, HI (US)

( * ) Notice: Subject to any disclaimer, the term of this patent is extended or adjusted under 35 U.S.C. 154(b) by 439 days.

(21) Appl. No.: 11/066,621

(22) Filed: Feb. 25, 2005

(65) Prior Publication Data

US 2006/0035975 A1 Feb. 16, 2006

Related U.S. Application Data

(60) Provisional application No. 60/547,909, filed on Feb. 26, 2004.

(51) Int. Cl.
*A61K 33/42* (2006.01)
*A61K 31/08* (2006.01)

(52) U.S. Cl. ............ 424/606; 514/723; 514/53; 514/57; 514/312; 424/78.38; 424/601; 424/692; 424/738

(58) Field of Classification Search ........ 514/566, 514/560; 424/464, 474
See application file for complete search history.

(56) References Cited

U.S. PATENT DOCUMENTS

| 3,838,196 | A | * | 9/1974 | Mercer | 514/566 |
|---|---|---|---|---|---|
| 5,602,180 | A | * | 2/1997 | Bennett | 514/578 |
| 5,605,885 | A | * | 2/1997 | Bernton et al. | 514/12 |
| 5,688,981 | A | * | 11/1997 | Nonomura | 556/116 |
| 5,797,898 | A | * | 8/1998 | Santini et al. | 604/890.1 |
| 6,114,387 | A | * | 9/2000 | Cutler | 514/562 |
| 6,123,965 | A | * | 9/2000 | Jacob et al. | 424/489 |
| 6,368,586 | B1 | * | 4/2002 | Jacob et al. | 424/78.08 |
| 6,538,155 | B1 | * | 3/2003 | Melman | 562/566 |
| 6,720,356 | B2 | * | 4/2004 | Feldman | 514/566 |
| 6,951,890 | B2 | * | 10/2005 | Cooper et al. | 514/673 |
| 2002/0182585 | A1 | * | 12/2002 | Kindness et al. | 435/4 |
| 2003/0198619 | A1 | * | 10/2003 | Dong et al. | 424/85.7 |
| 2005/0112200 | A1 | * | 5/2005 | Grossman et al. | 424/469 |
| 2005/0208119 | A1 | * | 9/2005 | Takemoto | 424/450 |
| 2005/0260262 | A1 | * | 11/2005 | Dansereau et al. | 424/464 |
| 2006/0264510 | A1 | * | 11/2006 | Halstead et al. | 514/566 |

FOREIGN PATENT DOCUMENTS

WO WO 00/16741 * 3/2000

* cited by examiner

*Primary Examiner*—Brian-Yong S Kwon

(57) ABSTRACT

A treatment protocol by which a renal stone patient is administered a chelating agent, generally once a day and preferably by mouth, during a treatment phase and is later administered the same chelating agent once a week, during a "maintenance" phase. The chelating agent is most preferably ethylene diamine tetraacetic acid (EDTA) and may be provided in a dosage form having an enteric coating and at least one external cathode and at least one external anode to create a galvanic current upon contact of the dosage form with the patient's intestinal contents.

15 Claims, 1 Drawing Sheet

ENTERIC COATED ORAL PHARMACEUTICAL TO ERODE KIDNEY STONES

BACKGROUND OF THE INVENTION

1. Field of the Invention

The invention relates to an oral treatment to reduce or to eliminate kidney stones, and to reduce the likelihood of their recurrence with a maintenance oral therapy.

2. Description of Related Art

Kidney stones represent a widespread, painful medical problem that is believed to have increased over the last few decades, particularly among Caucasian males in the United States and other predominantly Caucasian-populated nations. The most common type of kidney stone, or renal stone, is idiopathic in origin and generally calcareous. In contrast to the normal biomineralization of bones and teeth, the calcium oxalate biomineralization which is believed to cause renal stones contributes significantly to the cost of health care in the United States. Problems associated with renal stones not only include the perception of pain in the afflicted patient, but also mechanical irritation and compromise of renal tissue, back-pressure from restricted urine flow, and risk of infection due to mechanical irritation or back-pressure or to the mere presence of a foreign body in the kidney.

Ironically, it is believed that crystallization within the urinary tract occurs on an ongoing basis, with the formation of small crystals' providing the usual excretory function for eliminating calcareous stone salts. It is when such crystallization is not restricted to the urinary tract that the formation of unwanted crystalline stones in the kidney occurs. There are various theories as to why the crystallization is not restricted to the urinary tract in certain individuals, including genetic and dietary causes, but ultimately the cause of renal stones is not fundamentally understood. This idiopathy of renal stones creates unique challenges in developing effective treatments, because a general treatment must be able to reverse formations potentially attributable to a variety of causes.

Known methods of treating kidney stones include lithotripsy, chemical irrigation for partial or complete dissolution, surgical interventions and other techniques. Lithotripsy alone is performed on about 500,000 residents of the United States every year, and the costs involved in this lithotripsy medical care and concomitant lost productivity are enormous. Other pharmaceutical compositions have been developed for treating kidney stones, with an emphasis in the historic literature on citric acid and citrate-derivatives as potentially useful to dissolve calcareous formations, presumably due to acid solubilization of the salts.

A need remains for a simple, oral outpatient treatment to reduce the size or presence of kidney stones and, on a maintenance basis, to discourage their recurrence.

SUMMARY OF THE INVENTION

In order to meet this need, the present invention is a treatment protocol by which a patient is administered a chelating agent, generally once a day and preferably by mouth, during a treating phase. After the treating phase, a later maintenance phase administers the same chelating agent less frequently, usually once per week. The chelating agent is most preferably ethylene diamine tetraacetic acid (EDTA) but may be any chelating agent. The chelating agent is generally administered to the patient in the amount of 100 mg to 3-5 g, or even 10 g, per day during the treating phase, and generally speaking in the amount of about 1 g per week during the maintenance phase. Nutritional supplementation with 500-1500 mg each of calcium and potassium, or more preferably an adult multivitamin/mineral supplement, is important especially during the treating phase to prevent unwanted tooth and bone loss. Alternative compositions to the EDTA include, without limitation, ethylene diamine alone, porphine, and dimercaprol, but the administration of EDTA is preferred. In the most preferred embodiment of the invention, the chelating agent is administered in an enteric coated oral dosage form which is further provided with controlled-release anode-cathode materials in its outer surface, which anode-cathode materials create a galvanic current in response to the chemistry of the intestinal contents and which galvanic current in turn enhances delivery of the chelating agent through the intestinal wall.

DESCRIPTION OF THE PREFERRED EMBODIMENT(S)

Figure 1:
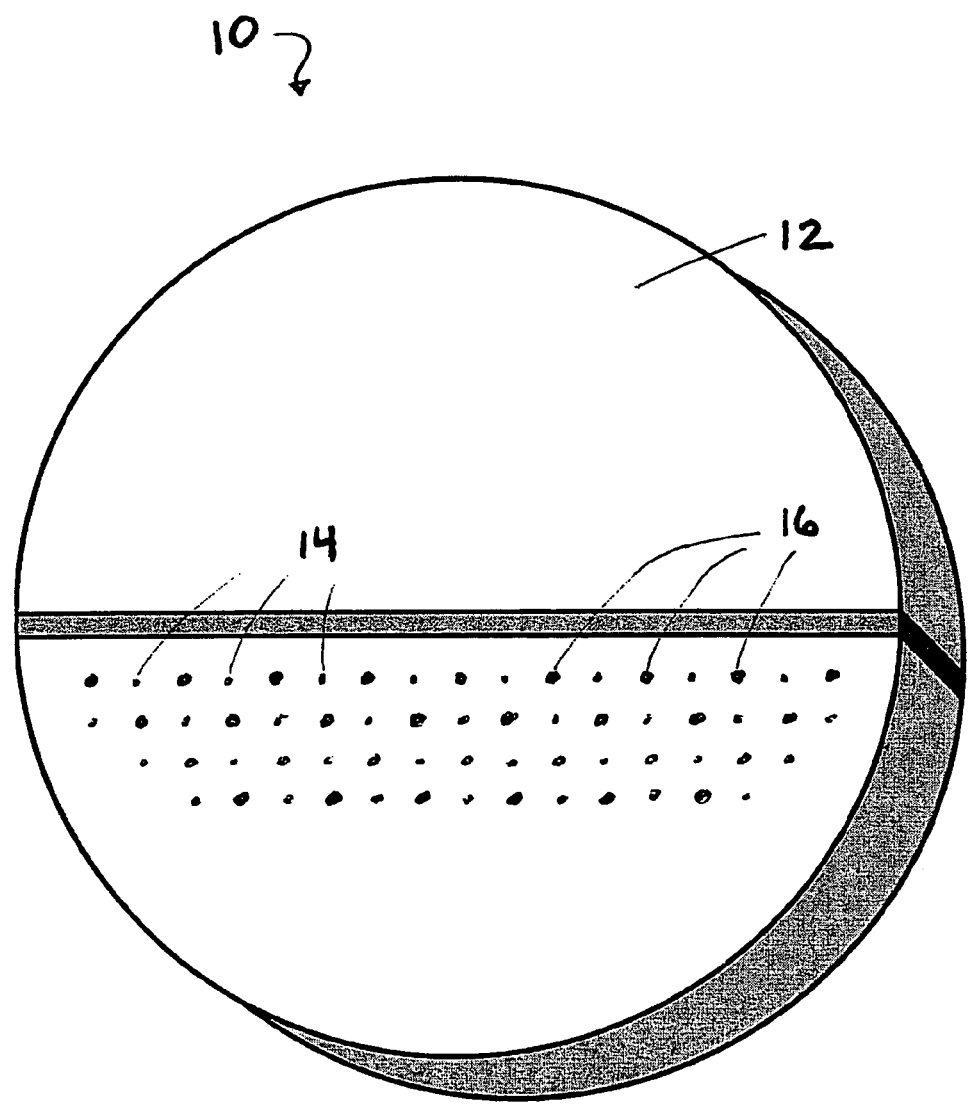
FIG. 1 is a perspective view of the most preferred embodiment of the invention in which the chelating agent is contained within an enteric coated dosage form (tablet) provided with anode and cathode functionality on its outer surface.

The present invention is a treatment protocol by which a patient is administered a chelating agent, generally once a day and preferably by mouth, during a treating phase which lasts days, weeks or three or six months. After the treating phase, a "maintenance" phase involves administration of the same therapeutic amount of a chelating agent but generally once a week rather than once per day. The chelating agent is most preferably ethylene diamine tetraacetic acid (EDTA) but may be any chelating agent. The chelating agent is generally administered to the patient in the amount of 100 mg to 3-5 g, or even 10 g, per day during the treating phase, and generally in the amount of about 1 g per week during the maintenance phase. Nutritional supplementation with 500-1500 mg each of calcium and potassium, or more preferably an adult multivitamin/mineral supplement, is important especially during the treating phase to prevent unwanted tooth and bone loss or other nutritional compromise. Alternative compositions to the EDTA include, without limitation, ethylene diamine alone, porphine, and dimercaprol, but the administration of EDTA is preferred. In the most preferred embodiment of the invention, the chelating agent is administered in an enteric coated oral dosage form which is further provided with controlled-release anode-cathode materials in its outer surface, which anode-cathode materials create a galvanic current in response to the chemistry of the intestinal contents and which galvanic current in turn enhances delivery of the chelating agent through the intestinal wall.

Determination of the dose of administration of the EDTA or other chelating agent is a function of the patient's ability to tolerate the therapy. The idea behind the present invention is to expose the kidneys to as large a concentration of EDTA (or other chelating agent) as possible to dissolve the calcareous stones in the shortest possible treating period. For this reason, the dose is best determined on an individual basis, to provide a high dose of chelating agent which is just short of the dose that causes gastrointestinal distress. For example, a patient treated with initial doses of 10 g per day and who experiences gastrointestinal distress (including but not limited to diarrhea) would have the daily dose titrated downward until the gastrointestinal distress abates. Although the unpleasantness of possible temporary gastrointestinal discomfort is acknowledged herein, such temporary discomfort is preferable to the pain caused by renal stones and much more preferable to the discomfort and pain incident to invasive procedures to remove the stones.

Nutritional supplementation during the treating phase is important, because the chelation therapy removes nutrients from the gastrointestinal tract as well as from the bloodstream. At a minimum, nutritional supplementation with 500-1500 mg each of calcium and potassium daily is contemplated. Ideally, the patient should faithfully ingest an adult multi-vitamin/mineral supplement such as, but not limited to, a Centrum Silver type supplement, on a daily basis. By giving large daily doses of chelating agent during the treating phase but for as few days, weeks or months as possible, nutritional depletion is minimized.

Maintenance therapy generally involves a weekly oral dose rather than a daily dose, generally at the same level as was given as a daily dose during the treatment phase. Maintenance dosing may therefore range from 100 mg to 3-5 or even 10 g of chelating agent one time per week, preferably about 1 g once a week.

EDTA is the preferred chelating agent because its short term usage for reducing or eliminating renal stones is relatively benign and for other reasons identified below. Porphine is a chelating agent similar to ethylenediamine in that it forms bonds to a metal ion through nitrogen atoms, and it is the simplest of a class of chelating agents known as porphyrins. Generally, porphyrins are porphine based compounds in which some of the terminal hydrogens are substituted with other groups of atoms including methane groups and etc. A well known porphyrin chelate is, of course, heme. Dimercaprol is a chelating agent that was originally employed to treat the toxic effects of an arsenic-containing mustard gas called Lewisite (dichloro(2-chlorovinyl)arsine) which was used in World War I. Metals chelated by dimercaprol cannot be assimilated into living cells and are excreted by the body, so dimercaprol is effective to dissolve renal stones in a generally non-toxic way.

However, EDTA is without question the preferred active agent for oral treatment of kidney stones, not only because of its relatively benign effects but because of its ubiquitous use in foodstuffs and its concomitant widespread acceptance as safe to ingest. EDTA is used extensively as a stabilizing agent in the food industry, to deactivate enzymes which cause food spoilage and to promote color retention in products such as dried bananas, beans of various types including garbanzo beans, tinned and frozen seafood products including shrimp and clams, and delicate processed foods such as mashed potatoes and custard-based pie fillings. EDTA is also commonly found in potted meats and bottled sauces as a preservative.

It should be understood that whereas EDTA oral therapy is effective to reduce or to eliminate renal stones, it is not believed that EDTA oral therapy is indicated for the dissolution of larger stones in the bladder. Treating periods should generally not exceed six months, and more preferably are limited to three months or less.

In order to implement the most preferred embodiment of the invention, the chelating agent is prepared in an enteric coated dosage form. Enteric coated dosage forms are well known in the art and prevent dissolution of the dosage form in the stomach contents but only in the intestinal environment. Beyond simply an enteric coating, however, the most preferred embodiment of the present invention further comprises at least one anode and at least one cathode on the outer surface of the enteric coated dosage form. The anode and the cathode create, when in contact with the intestinal contents, a mild galvanic current which enhances delivery of the chelating agent through the intestinal wall. Most preferably, the anode and cathode components on the exterior surface of the enteric coated dosage form are silver and zinc metal particulates which have been partially embedded in a polypropylene erodible coating. Erodible coatings may be selected from the group consisting of polypropylene, polyethylene, polyethylene terephthalate, natural rubbers, synthetic rubbers, copolymers, silicones, other polyalkylenes, or other suitable materials now known or hereafter developed in the art.

Referring now to FIG. 1, the erodible coating 12 of the dosage form (tablet) 10 includes a plurality of first metal particles 14 having an electrochemical potential and a plurality of second metal particles 16 having a different electrochemical potential from the plurality of first metal particles. The first particles 14 comprise pure or nearly pure silver, and/or suitable salts and oxides thereof. The second particles 16 comprise pure or nearly pure aluminum, cobalt, copper, gold, iron, magnesium, platinum, titanium or zinc, generally in metal but conceivably in suitable salt or oxide form as long as the electrochemical potential difference persists. The first metal particles 14 and second metal particles 16 are arranged alternatively within the erodible coating, wherein a sustained-release galvanic current is produced between the first metal particles and the second metal particles when the carrier layer is subjected to intestinal electrolytes. Although in FIG. 1 only a portion of the tablet surface contains the particles 14 and 16, any portion of the dosage form surface—or the entire surface—may bear the particles 14 and 16, in any pattern, as long as a galvanic current results. The first and second metal particles are spaced between 0.1 mm to 7.0 mm apart, but preferably are spaced less than 2.0 mm apart. The sustained galvanic current produced in the area at the surface of the dosage form 10 is between 0.1 to 1.0 millivolts, but preferably is about 0.2 millivolts. The drug-delivery enhancement afforded by the galvanic current will be understood by those skilled in the art to be iontophoretic.

Although the invention has been described with particularity above, with reference to particular chelating agents, dosages and routes of administration, the invention is only to be limited insofar as is set forth in the accompanying claims.

The invention claimed is:

1. A pharmaceutical composition for oral administration consisting essentially of ethylenediamine tetraacetic acid together with at least one pharmaceutically acceptable excipient prepared within an enteric coated dosage form, wherein at least one cathode and one anode protrude from the surface thereof, wherein the anode and the cathode create, when in contact with the intestinal contents, a mild galvanic current which enhances delivery of said ethylenediamine tetraaccetic acid (EDTA) through the intestinal wall.

2. The pharmaceutical composition according to claim 1, where said ethylenediamine tetraacetic acid and said pharmaceutically acceptable excipient are prepared within a dosage form selected from the group consisting of a capsule, a tablet and a caplet.

3. The enteric coated pharmaceutical composition according to claim 1, wherein said cathode and anode comprise one or more silver particles and one or more zinc particles partially embedded within said enteric coating.

4. The enteric coated pharmaceutical composition according to claim 1, wherein the enteric coating is an erodible coating selected from the group consisting of polypropylene, polyethylene, polyethylene terephthalate, rubbers, copolymers, silicones, and other polyalkylenes.

5. The enteric coated pharmaceutical composition according to claim 1 administered to a renal stone patient wherein the dosage of ethylenediarnine tetraacetic acid prepared in said composition ranges from 100 mg to 10 grams.

6. The enteric coated pharmaceutical composition according to claim 1, wherein the dosage form is selected from a group consisting of a capsule, a tablet and a caplet.

7. A method for reducing the formation of or the presence of renal stones, comprising administering, in unit dosage form, a composition according to claim 1 in an amount effective to reduce the formation or the presence of renal stones in an animal or human in need of such treatment.

8. The method according to claim 7, wherein a daily dose during an initial treating phase is between 100 mg and 10 g per day.

9. The method according to claim 8, wherein the daily dose during an initial treating phase is between about 1-5 g per day.

10. The method according to claim 9, wherein the daily dose during an initial treating phase is about 1 g per day.

11. The method according to claim 10, wherein, following an initial treating phase, a maintenance phase is instituted in which the animal or patient is administered between about 100 mg and 10 g ethylene diamine tetraacetic acid approximately once a week.

12. The method according to claim 11, wherein the maintenance phase dosage is about 1 g per week.

13. A method for the treatment of renal stones, comprising the oral administration of a pharmaceutical composition according to claim 1 to an animal or human in need of such treatment.

14. The method of claim 13, where said ethylenediamine tetraacetic acid and said pharmaceutically acceptable excipient are prepared within an enteric coated dosage form selected from the group consisting of a capsule, a tablet and a caplet.

15. The method of claim 13 wherein the dosage of ethylenediamine tetraacetic acid administered daily ranges from 100 mg to 10 grams.

* * * * *